US012672853B2

(12) United States Patent
Egorov

(10) Patent No.: US 12,672,853 B2
(45) Date of Patent: Jul. 7, 2026

(54) METHOD AND PROBE FOR PREDICTING SPONTANEOUS PRETERM DELIVERY

(71) Applicant: Advanced Tactile Imaging Inc., Ewing Township, NJ (US)

(72) Inventor: Vladimir Egorov, Princeton, NJ (US)

(73) Assignee: Advanced Tactile Imaging, Inc., Ewing, NJ (US)

( * ) Notice: Subject to any disclaimer, the term of this patent is extended or adjusted under 35 U.S.C. 154(b) by 27 days.

(21) Appl. No.: 18/395,293

(22) Filed: Dec. 22, 2023

(65) Prior Publication Data

US 2024/0122575 A1     Apr. 18, 2024

Related U.S. Application Data

(63) Continuation-in-part of application No. 16/574,270, filed on Sep. 18, 2019, now abandoned.

(51) Int. Cl.
| | |
|---|---|
| *A61B 8/00* | (2006.01) |
| *A61B 8/12* | (2006.01) |
| *A61B 90/00* | (2016.01) |

(52) U.S. Cl.
CPC ............... *A61B 8/485* (2013.01); *A61B 8/12* (2013.01); *A61B 8/4281* (2013.01); *A61B 8/4422* (2013.01); *A61B 8/4455* (2013.01); *A61B 8/4483* (2013.01); *A61B 8/5223* (2013.01); *A61B 90/06* (2016.02); *A61B 2090/064* (2016.02)

(58) Field of Classification Search
None
See application file for complete search history.

(56) References Cited

U.S. PATENT DOCUMENTS

| | | | |
|---|---|---|---|
| 5,265,612 A | 11/1993 | Sarvazyan | |
| 6,511,427 B1 * | 1/2003 | Sliwa, Jr. ............... | A61B 8/429 |
| | | | 600/459 |
| 8,052,622 B2 | 11/2011 | Egorov | |
| 8,187,208 B2 | 5/2012 | Egorov | |
| 8,419,659 B2 | 4/2013 | Egorov | |
| 8,840,571 B2 | 9/2014 | Egorov | |
| 2006/0025682 A1 | 2/2006 | Vanderby | |
| 2007/0239011 A1 | 10/2007 | Lau | |
| 2008/0269606 A1 | 10/2008 | Matsumura | |
| 2013/0253318 A1 * | 9/2013 | Eskandari .............. | A61B 8/587 |
| | | | 600/438 |
| 2015/0032032 A1 * | 1/2015 | Egorov ................ | A61B 5/4343 |
| | | | 600/591 |
| 2016/0166233 A1 * | 6/2016 | Yoo .......................... | A61B 8/12 |
| | | | 600/463 |

OTHER PUBLICATIONS

Wozniak S et al. Elastography for predicting preterm delivery in patients with short cervical length at 18-22 weeks of gestation: a prospective observational study. Ginekol Pol. 86; 442-447, 2015.

* cited by examiner

*Primary Examiner* — Shahdeep Mohammed
(74) *Attorney, Agent, or Firm* — Boris Leschinsky

(57) ABSTRACT

A cervix probe is equipped with a tactile sensor array and an ultrasound transducer and configured for simultaneous acquisition of stress data and ultrasound strain data for the same sector of the cervix. Acquired and recorded stress and strain data are transmitted to a data processor for calculating cervix elasticity and cervix length, followed by calculating a probability of spontaneous preterm delivery using a clinically validated predictive model.

14 Claims, 8 Drawing Sheets

101   102   103   104   105

106   107   108   109   110

111

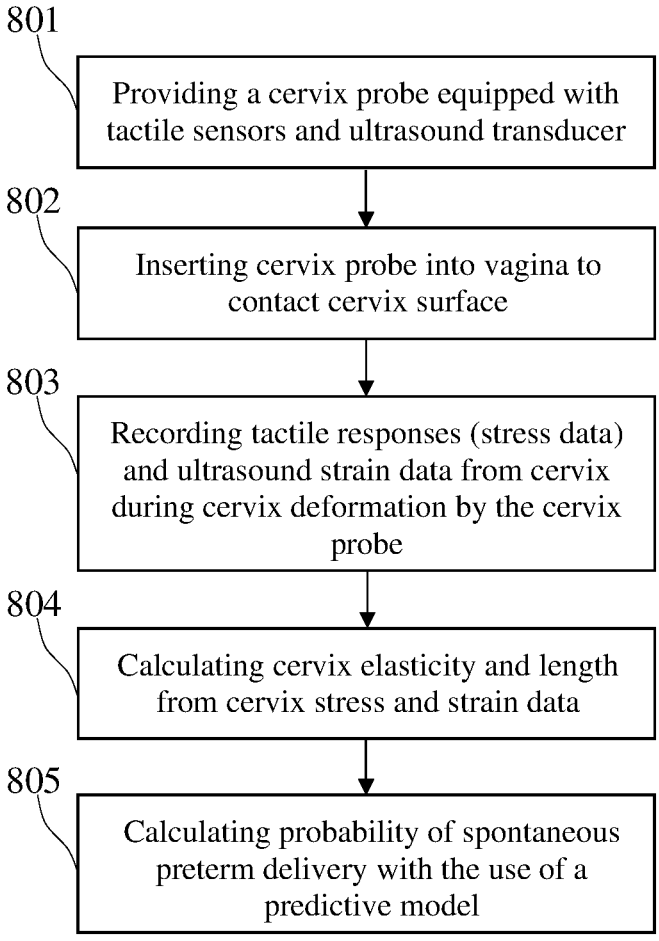

801

Providing a cervix probe equipped with tactile sensors and ultrasound transducer

802

Inserting cervix probe into vagina to contact cervix surface

803

Recording tactile responses (stress data) and ultrasound strain data from cervix during cervix deformation by the cervix probe

804

Calculating cervix elasticity and length from cervix stress and strain data

805

Calculating probability of spontaneous preterm delivery with the use of a predictive model

FIG. 8

METHOD AND PROBE FOR PREDICTING SPONTANEOUS PRETERM DELIVERY

CROSS-REFERENCE TO RELATED APPLICATIONS

This patent application is a continuation-in-part of the co-pending U.S. patent application Ser. No. 16/574,270 filed 18 Sep. 2019, which in turn is a continuation-in-part of U.S. patent application Ser. No. 15/249,672 filed 29 Aug. 2016 with the same title and by the same inventor and entitled METHODS AND PROBES FOR VAGINAL TACTILE AND ULTRASOUND IMAGING, currently abandoned, which in turn claims a priority benefit from a U.S. Provisional Patent Application No. 62/215,227 filed 8 Sep. 2015 with the same title. All documents are incorporated herein in their respective entireties by reference.

GOVERNMENT-SUPPORTED RESEARCH

This invention was made with the US Government support under grant No. R43HD090793 awarded by Eunice Kennedy Shriver National Institute of Child Health & Human Development, USA. The Government has certain rights in this invention.

FIELD OF THE INVENTION

The present invention generally relates to cervix characterization of pregnant women. Specifically, the invention describes methods and devices for detecting conditions leading to spontaneous preterm delivery.

BACKGROUND

Preterm birth is a leading global cause of neonatal mortality despite intensive research and numerous advances in perinatal medicine. Almost 1 million children die each year due to complications of preterm birth. In almost all countries that have reliable data, preterm birth rates are increasing. Of the 14 million survivors per year, many face a lifetime of disability, including learning disabilities, visual and hearing impairments. The morbidities include respiratory distress syndrome, bronchopulmonary dysplasia, intraventricular hemorrhage, periventricular leukomalacia, necrotizing enterocolitis, sepsis, and retinopathy of prematurity. Long-term complications include cognitive disorders, behavioral problems, and cerebral palsy. These consequences imply devastating financial, social, and emotional effects on the parents or the affected children.

The overall preterm birth rate peaked in the U.S. in 2006 at 12.8% and fell by 14% each year until 2014, a decrease attributed by some to a remarkably successful campaign to reduce the number of teenage pregnancies. However, it has risen again over the past two years and now stands at 9.8%, which is higher than most European countries where preterm birth rates vary from 5% to 9%.

A preterm birth is defined by the World Health Organization as a birth before 37 completed weeks of gestation or fewer than 259 days since the first day of a woman's last menstrual period. Preterm births occur for a variety of reasons. Most preterm births happen spontaneously. Common causes of a spontaneous preterm delivery (SPTD) include multiple pregnancies, infections, chronic conditions, lifestyle, family history, cervical incompetence. However, often no single cause is identified. Although SPTD is often a multifactorial event, precocious cervical softening, shortening and dilatation are a common denominator.

Clinical risk factors for SPTD include obstetric history (familial genetic predisposition, uterine malformation, previous preterm labor, previous cervical surgery) and other aspects of the current pregnancy (multifetal gestation, genital tract bleeding and/or infection, fetal malformation, preterm rupture of membranes, shortened cervix, and other pregnancy complications including preeclampsia and gestational diabetes mellitus). A previous preterm birth before 34 weeks' gestation is one of the strongest risk factors for subsequent preterm birth. However, insofar as nulliparous women have no past obstetric history to call upon, any such previous history risk factor-based assessment is not applicable in their situation. Overall SPTD risk factors assessment alone is unreliable.

Extensive cervical remodeling is needed for the cervix to dilate and pass a fetus fully. While human parturition is not completely understood, it is a complex system that involves interactions between placental, fetal, and maternal mechanisms. The extracellular matrix of the cervix is primarily made up of tightly packed collagen bundles. Gradually, throughout the pregnancy, the composition of the cervix changes as the collagen density decreases, in addition to realignment and degradation of collagen cross-linking due to proteolytic enzymes, and an increase in the hyaluronic acid and water content. Further, through a cascade of events, inflammatory mediators increase the production of prostaglandins. Prostaglandins invading the cervix mediate the release of metalloproteases that further break down collagen and change the cervical structure. Cervical softening and distention results from these extracellular matrix compositional changes, specifically, increased vascularity and stromal and glandular hypertrophy, and are due, in part, to an increase in collagen solubility closer to delivery.

The cervical elasticity assessment currently used in clinical practice is relying on a clinician's evaluation of the cervix as 'hard,' 'medium' or 'soft,' which is descriptive and subjective. Clinicians use terms such as 'softening,' 'shortening,' 'funneling,' and 'effacing' to describe the changes in the cervical conditions that occur during pregnancy. Elasticity (consistency) is a component of the Bishop score [Bishop E H. Pelvic scoring for elective induction. Obstetrics Gynecology 1964; 24: 266-8] that also includes dilation, effacement, station, and position, and is used basically to predict the success of induction of labor. The highest possible total Bishop score is 13, and the lowest possible score is 0. A Bishop score of 8 or greater is favorable for induction, or the chance of a vaginal delivery with induction and is similar to spontaneous labor. The cervical score described by Houlton in 1982 Moulton M C C, Marivate M, Philpott R H. Factors associated with preterm labour and changes in the cervix before labour in twin pregnancy. Br J Obstet Gynaecology 1982; 89: 190-194.] places a greater emphasis on cervical length. However, digital cervical score and Bishop score as predictors of SPTD demonstrated poor diagnostic accuracy.

The uterine cervix must provide structural integrity and mechanical resistance to ensure normal development of the fetus as the uterus expands to accommodate the fetus' growth. Preterm delivery is closely related to a premature cervical ripening. The scientific premise for the invention is that the elasticity of a cervix is a sensitive parameter characterizing the stage of cervical conditions (ripening). The risk of spontaneous preterm delivery is increased in women who are found to have a short cervix by vaginal ultrasonography during pregnancy. Therefore, assessment of cervix by a device measuring cervical elasticity and cervical length may provide an adequate approach for identifying pregnant women at high risk of SPTD.

The current invention disclosures a new device, referred to as a Cervix Monitor (CM), for detecting cervix conditions leading to SPTD and calculating probability of SPDF. The discovery and implementation into the clinical practice of novel biomarkers that could reliably identify women who will subsequently deliver preterm may enable timely medical attention and targeted therapeutic treatments aimed at improving maternal and fetal outcomes. The expected clinical impact may be significant for the considerable financial burden that it might reduce, not just for the health care system in the short term, but for the long-term care for the individual, the family, and the society.

SUMMARY

The object of the present invention is to overcome the drawbacks of the prior art and to provide novel methods and devices for objective biomechanical characterization of the cervix of pregnant women. Specifically, this invention discloses novel methods and devices for detection of cervix conditions leading to spontaneous preterm delivery. The Cervix Monitor (CM) may be designed to measure the stress applied to the cervix using a tactile sensor array used to acquire stress data and to measure a time-of-flight of an ultrasound pulse to internal cervical os (defining the opposite boundary of the cervix) using ultrasound transducer to acquire strain data. Tactile and ultrasound sensors may be located on a tip of the CM probe. Both stress and strain data allow the calculation of cervix elasticity and effacement (length). The CM probe may be connected to a portable data processing unit to allow easy transportation of the entire system and 24/7 readiness for cervix monitoring in a clinical setting.

Another object of the invention is to provide novel methods and devices for objective characterization and real-time visualization of biomechanical properties of a cervix in four sectors.

A further yet object of the invention is to provide novel methods and devices for acquisition of stress and strain data from a cervix to be used as input in a finite element model to describe biomechanical status of the cervix.

Another object of the invention is to provide novel methods and devices for objective visualization and real-time detection of a biomechanically weak sector of the cervix relative to an average cervix status.

Another yet object of the invention is to provide novel methods and devices for composing of a cervix tissue elasticity map using stress and strain data.

A further yet object of the invention is to provide novel methods and devices for objective diagnosis of spontaneous preterm conditions by comparing acquired tactile response data and ultrasound data for a particular patient against respective normal/diseased values obtained from clinical data collected from a number of patients with known clinical status.

In embodiments, a method for predicting spontaneous preterm delivery may include the steps of:
  a) providing a cervix probe equipped with a plurality of tactile sensors and an ultrasound transducer positioned adjacent thereto,
  b) inserting the cervix probe into a vagina along a vaginal canal to contact external cervix wall surface of a pregnant woman, c) simultaneously acquiring cervix stress data with the tactile sensors and cervix strain data with the ultrasound transducer for the same sector of cervix during cervical tissue deformations by the cervix probe, while avoiding detection of stress data of surrounding tissues, such as adjacent vaginal walls,
  d) calculating cervix elasticity and cervix length from the cervix stress data and cervix strain data, and
  e) calculating the probability of spontaneous preterm delivery with the use of the cervix elasticity and cervix length as inputs to a predictive model.

Additional method steps may include a series of repeated evaluations of the cervix status of a pregnant woman beginning from about 22 weeks of pregnancy, measurement of several (such as four) radially oriented cervix sectors (upper, lower, left and right), calculating cervix length from ultrasound pulse time-of-flight to internal os surface of the cervix, calculating cervix elasticity based on a finite element model or another computer simulation for cervix, comprising a cervix map with a set of predefined sectors each characterizing a respective measure of cervix elasticity and length data in this sector, as well as comprising a predictive model derived from a clinical validation study.

A novel probe for predicting spontaneous preterm delivery may include:
  a front head equipped with a flat, cervix-facing plurality of tactile sensors forming a tactile array,
  the head being suitably shaped for contacting a cervix surface perpendicular to the internal os surface of the cervix, and avoid detecting compression of adjacent vaginal walls or other tissues surrounding the cervix,
  the plurality of tactile sensors forming together a flat tactile sensor array located over at least some of the cervix-facing head surface of the probe,
  an ultrasound transducer located adjacent to or in the center of the plurality of tactile sensors on the same front-facing surface of the probe head,
  wherein the tactile sensor array is configured to acquire stress signals and the ultrasound transducer is configured to emit an ultrasound pulse and to acquire a scattered ultrasound waveform from soft tissues of cervix for the same sector of cervix, while avoiding detection of stress of any tis sued other than the cervix,
  a control unit operably connected to the tactile sensors and the ultrasound transducer and configured for acquiring the stress data from tactile sensors and the scattered ultrasound waveform from ultrasound transducer, and
  a data processor operably connected to the control unit and configured for calculating cervix elasticity and cervix length from stress data and ultrasound waveforms and calculating of probability of spontaneous preterm delivery.

In embodiments, a cervix-facing surface of the probe head may include a durable elastic medical grade silicone layer to allow for stress transmission via reversible deformation thereof from the cervix-facing surface to tactile sensors located underneath. This allows for multiple disinfections of the probe. The ultrasound transducer may be made using a piezoceramic composite material with a mylar film as an acoustic matching layer between an ultrasound transducer and front-facing surface, and a silicone backing layer behind the ultrasound transducer.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 8 presents a block-diagram of the steps of the method for predicting spontaneous preterm delivery.

DETAILED DESCRIPTION OF THE INVENTION

Figure 1:
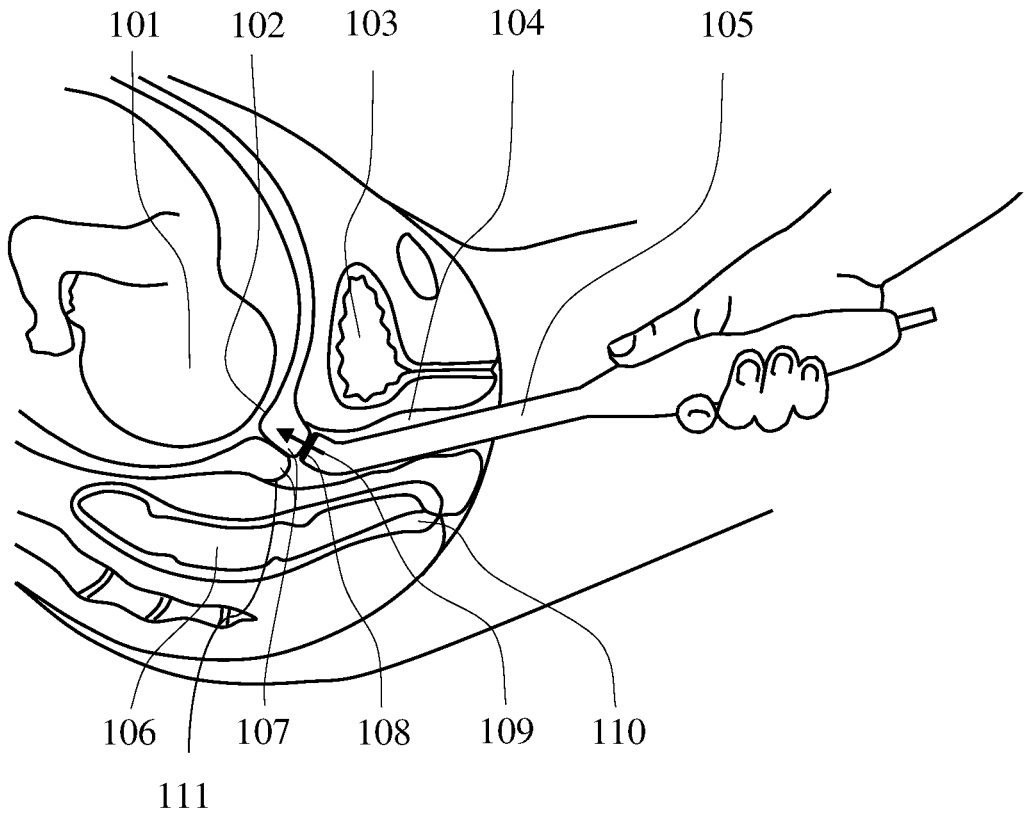
FIG. 1 illustrates a cervix probe location during acquisition of stress and ultrasound strain data from cervix using cervix deformation along the black arrow.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows:

"tactile sensor" is the sensor capable of measuring an applied force averaged per sensor area or pressure;

"ultrasound transducer" is the sensor capable to emit and receive an acoustic wave;

"stress" is a force per unit of area (pressure) measured at the external surface of cervix facing the vagina;

"strain" is a soft tissue displacement under tissue deformation;

FIG. 1 illustrates a cervix probe 105 location during the acquisition of stress and strain data from a cervix 107 at cervix deformation with the probe head 108 oriented along arrow 109. Shown in FIG. 1 is a sagittal cross-section of the pelvic floor of a pregnant woman with a fetus 101. The pelvic landmarks are a bladder 103, a vagina 104, a rectal canal 106 with anus 110. The probe head 108 may have a flat surface with tactile sensors and ultrasound transducers configured to face and deform the external wall of the cervix 107 at the external os 111 and not the walls of the vagina 104, either directly or through an elastic protective layer. The probe head 108 may be designed to have sensors in contact with the entire external wall of the cervix 107 or individual parts thereof. In other embodiments, the head 108 may include groups of sensors designed to contact individual sectors of the external os 111 of the cervix 107; such as 2 sectors, 3 sectors, 4 sectors, 5 sectors, 6 sectors, 7 sectors, 8 sectors, 9 sectors, 10 sectors, as the invention is not limited in this regard. The following description uses a four-sector exemplary approach for characterization of the cervix (upper, lower, and two lateral sectors of the cervix).

FIG. 1 further shows the probe head 108 paced in contact with the upper cervix sector. The size of the head 108 and location of the sensors may be arranged for the head to be used to characterize the entire cervix all at once, or alternatively for characterizing each desired sector or groups of adjacent sectors of the cervix at a time.

A front portion of probe head 108 containing sensors may be suitably shaped for contacting the external wall of the cervix at the external os 111 in a generally perpendicular direction to the internal os surface 102 of the cervix 107. It allows the acquisition of ultrasound-reflected signal from the internal os 102 and measuring a time-of-flight for the ultrasound-reflected signal. Taking into account the acoustic speed of about 1,540 m/s for soft human tissues, one may calculate the cervix length from internal os surface to the external cervix wall surface contacting the probe head 108. Changes in the time-of-flight during the cervix compression or deformation by the probe head 108 may be used to provide strain data for the respective cervix sector or a group of sectors currently under investigation. A plurality of tactile sensors (from 1 to 16 sensors) may be used to form together a tactile array located over at least a portion of the probe head 108, which may be configured to record stress data from cervix surface during cervical tissue deformation by the front portion of the probe 105. The tactile sensor array may include 1, 2, 3, 4, 5, 6, 7, 8, 9, 10, 11, 12, 13, 14, 15, or 16 suitable tactile sensors as the invention is not limited in this regard.

An ultrasound transducer may be located adjacent to the plurality of tactile sensors over the same front portion of the probe head 108. The tactile sensor array may be configured to acquire stress data in the form of pressure data on each tactile sensor while the ultrasound transducer may be configured to first emit an ultrasound pulse and then to acquire a scattered ultrasound waveform from soft tissues of the cervix including the internal os surface for the same sector of cervix. A control unit (not shown) may be operably connected to the tactile sensors array and to the ultrasound transducer. The control unit may further be configured for acquiring stress data from tactile sensors and a scattered ultrasound waveform data from the ultrasound transducer. A data processor (not shown) may be operably connected to the control unit and configured for calculating cervix elasticity and length from stress data and ultrasound waveforms.

Figure 2:
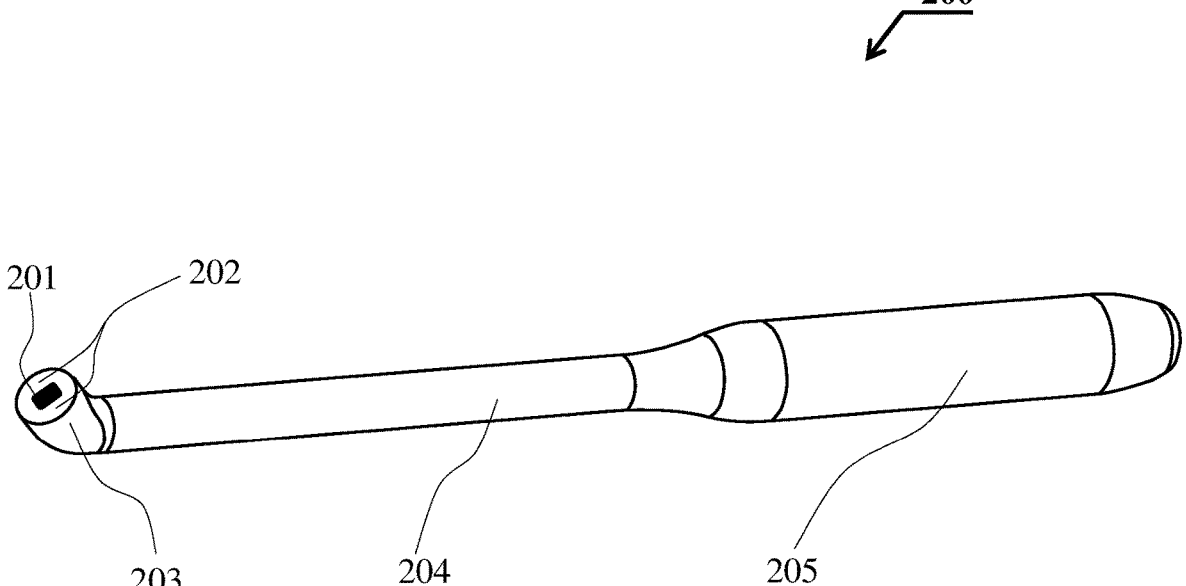
FIG. 2 shows an embodiment of a probe for predicting spontaneous preterm delivery.

FIG. 2 presents an exemplary embodiment of a probe 200 for predicting spontaneous preterm delivery. The probe 200 may comprise a handle 205, a shaft 204 and a head 203 with a flat surface configured for contacting cervix as shown in FIG. 1. The probe 200 may contain a tactile array 202 with a plurality of sensors (four in this case) and at least one ultrasound transducer 201 as shown in FIG. 2. In one embodiment, the ultrasound 5.0 MHz transducer 201 measuring about 3.5 mm in size may be configured for working in the pulse-echo mode with data acquisition resolution of about 20 ns (50 MHz sample rate). Biocompatible, two-component silicone (such as for example made by NuSil Technology, CA) may be employed to provide sensor assembly with a functional, durable and stable mechanical protection cover. A proprietary printed circuit board of a control unit may be designed to perform the dual functions of stress signal acquisition and generation/acquisition of synchronized ultrasound signals. Its key features are to operate and acquire data from the plurality of tactile sensors 202 and the ultrasound transducer 201 at about 100 data frames per second. The stress measurement noise level in this example is about 25 Pa within the operational range of 40 kPa. The ultrasound transmitting pulses have a peak amplitude below 50 V and a length of less than 1 μs, which provide acoustic power significantly below the limits established by the FDA for ultrasound emission in obstetrics: spatial-peak temporal-average $I_{spta}$=94 (mW/cm2), spatial-peak pulse-average intensity $I_{sppa}$=190 (W/cm2), and mechanical index MI=1.9.

Medical grade 316 stainless steel, used in the production of surgical instruments, may be used to fabricate the probe shaft 204 while biocompatible plastic materials may be used for probe handle 205 and a head 203. The device software interface may be configured to allow real-time observation of the cervical ultrasound signal as well as the level of applied stress. The ultrasound peak position for cervix internal os signal may be calculated with the use of a signal envelope after the Gaussian complex wavelet filtering at 5 MHz frequency. The cervical elasticity may be calculated as a stress/strain ratio of applied load to the cervix surface from the probe (stress) to the resultant changes in the cervical length (strain). This approach was validated with the soft tissue models in bench testing and verification. Young's modulus was calculated from the stress-strain data based on a semi-infinitive linear elastic model and based on a finite element modeling of the cervix deformation with the probe 200.

The cervix examination procedure may comprise the following four main steps:

(1) inserting the speculum into the vagina to provide appropriate visualization and access to the cervix;

(2) performing probe measurements by deforming various portions of the external cervix wall and not the vaginal walls, such as for example, at 3, 6, 9, and 12 o'clock, specifying the probe head location at the external os cervix surface and on a cervix map displayed to the user;

(3) reviewing of the measurement results (ultrasound reflected waves and applied loads), and (4) removal of the probe and speculum from the vagina.

Figure 3:
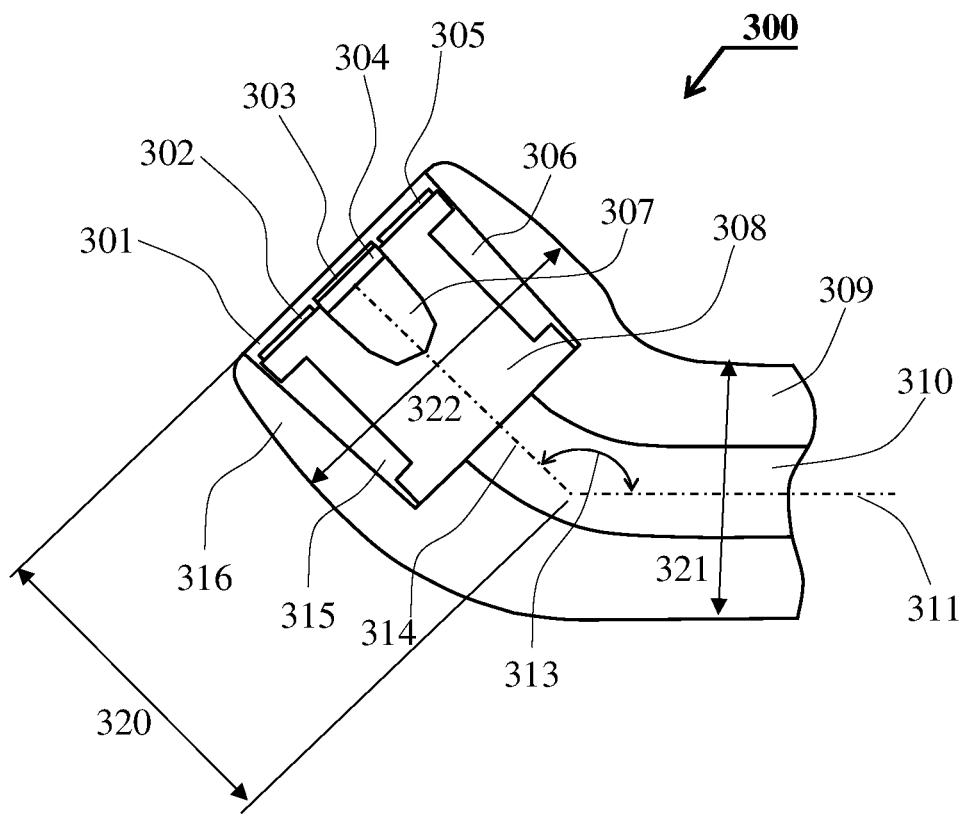
FIG. 3 shows a close-up cross-sectional view of a probe head with tactile and ultrasound transducers.

FIG. 3 presents an embodiment of a cervix probe with a head 300 equipped with tactile sensors 302 and 305 and an ultrasound transducer 304 for predicting spontaneous preterm delivery. The number of tactile sensors may be more than 2, as mentioned above. All tactile sensors may form a flat tactile array oriented to face the cervix and be positioned around the ultrasound transducer 304 and at the same plane therewith. The ultrasound transducer, in this case, may be placed in a geometrical center of the flat tactile array and aligned therewith for simultaneous and coordinated contact with the external cervix wall. Each individual tactile sensor may be made as a capacitive type sensor, although other force sensors may be used for the purposes of the invention.

The ultrasound transducer may be built from composite piezoceramic materials, for example, 1-3 composites, and may be characterized by lower acoustic impedances (for example ranging from about 5 MRayl to about 30 MRayl), high coupling coefficients (typically about 0.6 to about 0.75), high bandwidth and lower mechanical quality factor (Qm). The ultrasound transducer 304 may be covered with an acoustic matching layer 303 on the front side and a backing layer 307 on the back side. The matching layer 303 may be preferably made using a mylar film of 0.09 mm thickness for 6 MHz. The thickness of the matching layer 303 was optimized experimentally for other frequencies by maximizing scattered signal amplitude and minimizing signal length. The backing layer 307 may be filled by silicone with attenuation of about 20 dB/mm at 6 MHz in a cavity with a depth of about 5 mm located behind the ultrasound transducer 304. Both tactile sensors 302, 305 and the ultrasound transducer 304 may be positioned on a support base 308 placed inside the probe body 309 with a central cavity 310 extending therethrough for housing electrical wiring of the sensors and the transducer. After positioning of the support base 308 with assembled sensors and transducer therein in the suitably sized front opening of the probe body 309, it may be secured therein by filling the spaces 301, 306 and 315 with a medical grade silicone having acoustic impedance of about 1 MRayl. The thickness of a surface layer 301 covering the tactile sensors 302, 305 may be about 0.4 mm. The silicone layer 303 covering the ultrasound transducer 304 may be about 0.3 mm thick. The probe head 316 may have a diameter of about 10-12 mm.

The angle 313 between the probe central line in shaft 311 and central line 314 inside the probe head may be from about 130 degrees to about 150 degrees, such as about 140 degrees. This allows positioning of the probe head orthogonally to the cervix surface and, at the same time, allowing for an easy insertion of the probe into vagina and removal therefrom after the test procedure is complete.

Dimensions of the head 300 together with the tilt angle 313 may be selected to allow the head to exclusively deform the external cervix wall while avoiding deforming of adjacent vaginal walls. This is important and advantageous as compared to the prior art because it improves the accuracy of pressure distribution detection by avoiding detection of deformation of tissues other than the cervix. To that end, shaft diameter 321 may be selected to be from about 10 mm to 14 mm, such as about 12 mm; head diameter 322 may be selected to be from about 12 mm to 15 mm, such as about 14 mm; and head length 320 may be selected to be from about 14 mm to 20 mm, such as about 18 mm.

Figure 4:
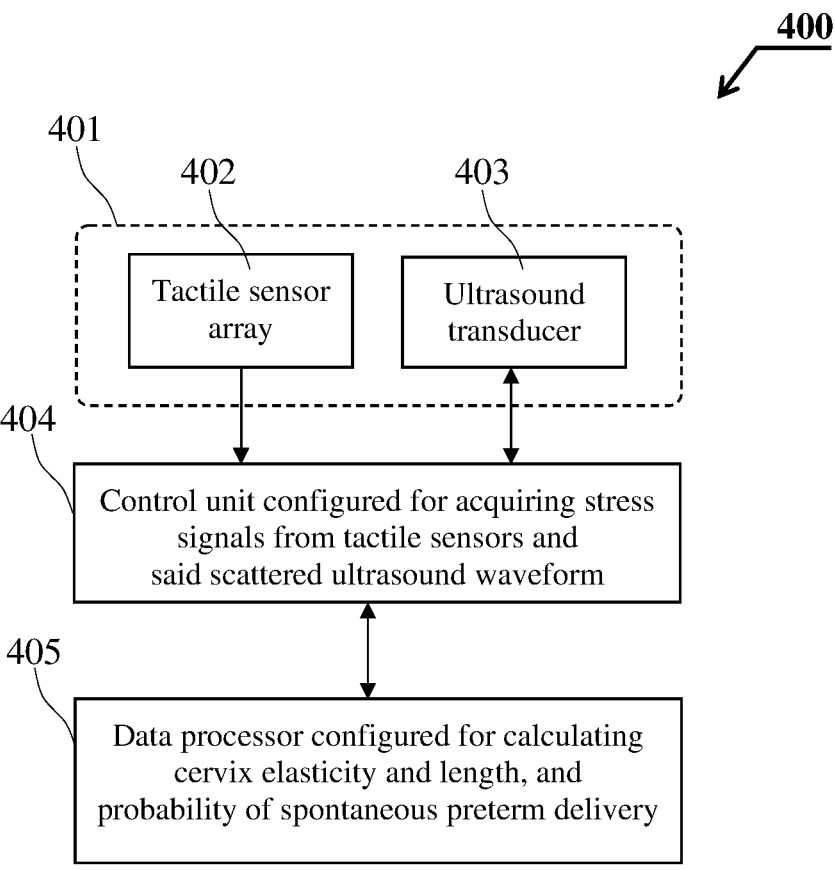
FIG. 4 presents a block-diagram of the probe of the present invention.

FIG. 4 presents a block-diagram of a system 400 for predicting spontaneous preterm delivery. A probe 401 comprises a plurality of tactile sensors 402 forming together a tactile sensor array located over at least a portion of the probe head. The probe 401 further comprises an ultrasound transducer 403 located adjacent to the plurality of tactile sensors on the same front surface. The tactile array 402 may be configured to acquire stress data and the ultrasound transducer 403 is configured to emit an ultrasound pulse and to acquire a scattered ultrasound waveform from soft tissues of cervix for the same sector of cervix. A control unit 404 may be operably connected to the tactile sensors 402 and the ultrasound transducer 403 and configured for acquiring the stress data from tactile sensors 402 and the scattered ultrasound waveform from ultrasound transducer 403. A data processor 405 is operably connected to the control unit 404 and configured for calculating cervix elasticity and length from stress data and ultrasound waveforms, which in turn may be used for calculating of probability of spontaneous preterm delivery.

Figure 5:
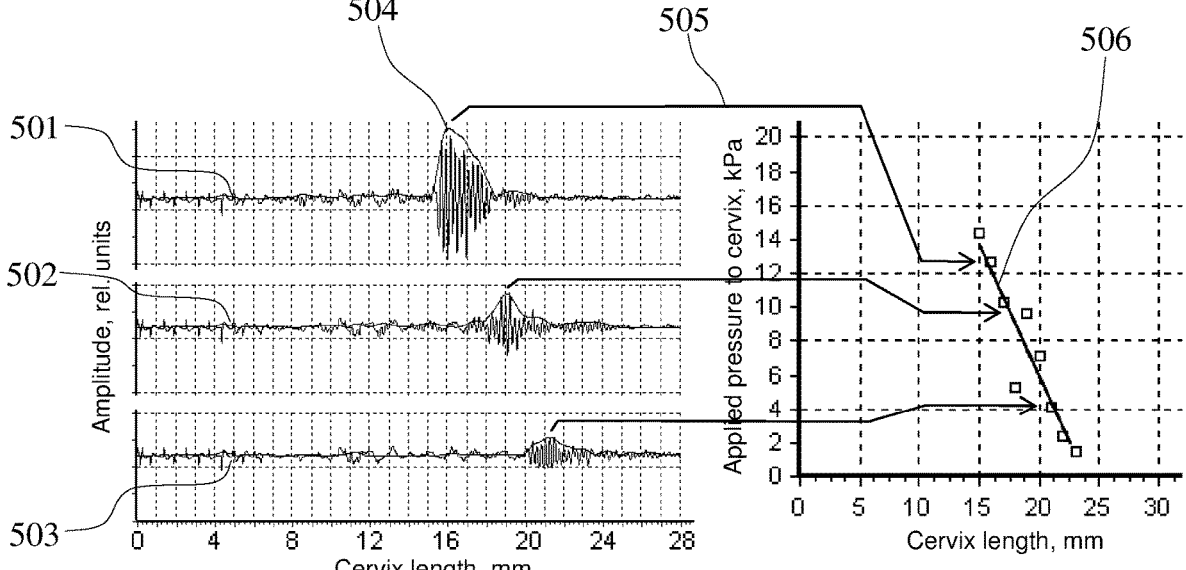
FIG. 5 shows a graph with ultrasound signals reflected from internal cervical os during cervix deformation by the probe (left panel) and stress-strain data (right panel) recorded for 32 y.o. woman at 25-week pregnancy.

FIG. 5 shows exemplary ultrasound signals 501-503 obtained from cervical tissue during cervix deformation by the probe (left panel) and a graph 506 of stress (pressure) versus strain (compression) data recorded for 32 y.o. woman at 25 weeks of pregnancy (right panel). The recorded ultrasound signals 501-503 had an identifiable peak amplitude 504 reflected from the cervix's internal os, which may be used for reproducible measurement of ultrasound time-of-flight and cervix length in mm as shown along the horizontal axis. The peak position was calculated with the use of a signal envelope lines (Gaussian complex wavelet filtering) as shown in the left panel of FIG. 5. Line 505 shows the translation of the peak position (cervix length) into stress-to-strain graph 506 on the right panel, which shows a graph of dependence of applied stress to the cervix in kPa from the cervix length during its deformation. The availability of stress-to-strain data allows the calculation of the cervix elasticity.

EXAMPLE

Figure 6:
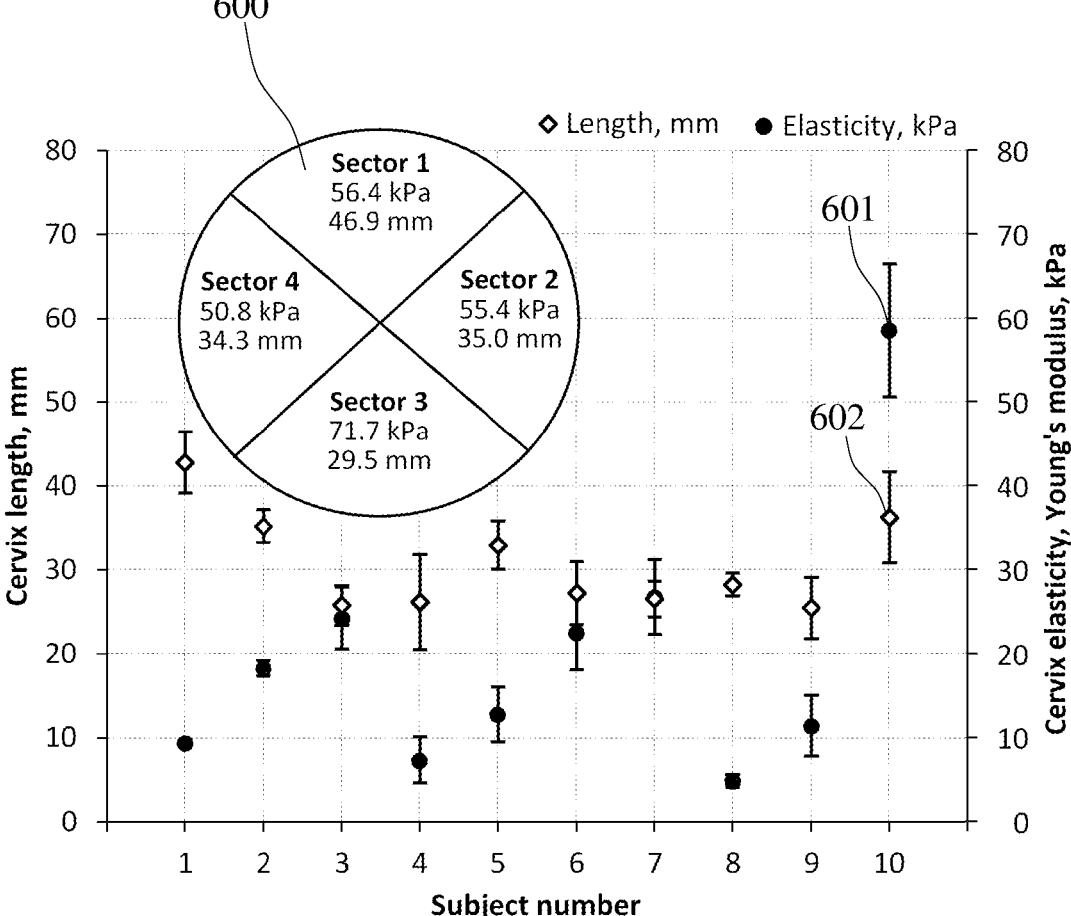
FIG. 6 shows clinical data for cervix elasticity and length for 10 pregnant women and cervix map for subject No. 10.

FIG. 6 shows clinical results of measured cervix elasticity and length for 10 pregnant women and a cervix map 600. The cervix map 600 may have a number of sectors, in this case four sectors. The results for subject No. 10 (tissue elasticity and length distribution per four sectors) are shown in cervix map 600. Average values and standard deviations (up/down bars) for cervical elasticity and length for 10 cases were calculated based on two measurements per each of the 4 sectors (8 measurements per case); the values were 19.7±15.4 kPa, and the length was 30.7±6.6 mm. Subject No. 10 had an average cervix elasticity 59 kPa (see position 601) and cervix length 36 mm (see position 602). The average standard deviation for the 4 cervix sector measurements of elasticity was found to be ±3.5 kPa and the length was ±3.4 mm.

Figure 7:
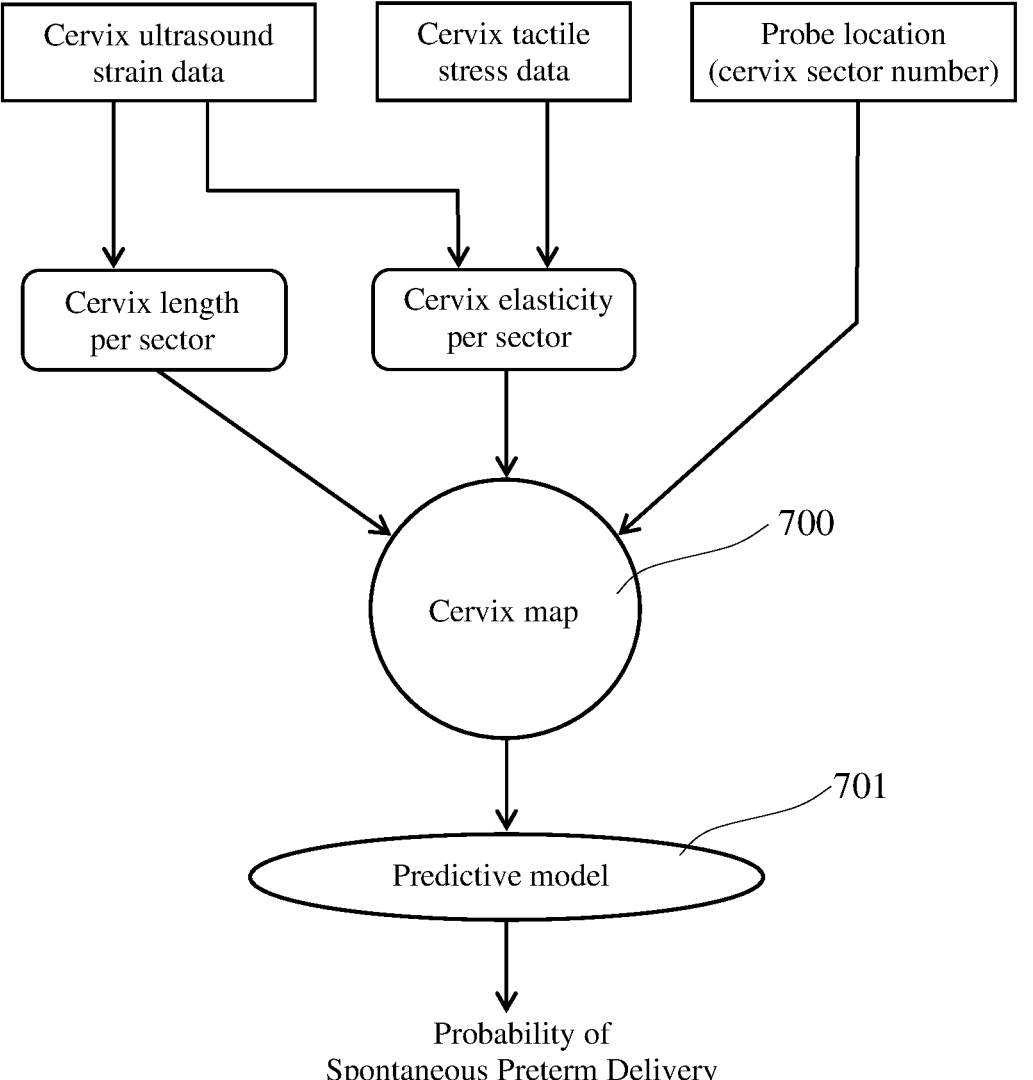
FIG. 7 presents a data flow chart of a method for predicting spontaneous preterm delivery.

FIG. 7 presents a data flow chart of a novel method for predicting spontaneous preterm delivery. This method includes:

a) acquisition of cervix stress and strain data for a plurality of cervix sectors, b) calculating cervix length by approximating the strain data to zero cervix deformation (see FIG. 5), c) calculating cervix elasticity using the cervix strain data and the cervix stress data, d) using the cervix length and cervix elasticity data from a cervix map 700 as inputs for a predictive model 701, and e) calculating the probability of spontaneous preterm delivery. The predictive model 701 may be composed using a statistical or neural network classifier based on results of a clinical validation study.

FIG. 8 presents a block diagram of a method for predicting spontaneous preterm delivery, comprising:

step 801 of providing a cervix probe equipped with a plurality of tactile sensors and an ultrasound transducer positioned adjacent thereto, step 802 of inserting the cervix probe into a vagina along a vaginal canal to contact cervix surface of a pregnant woman, step 803 of simultaneously recording/acquiring cervix stress data using the tactile sensors and ultrasound cervix strain data for the same sector of the cervix during cervical tissue deformations by the cervix probe, step 804 of calculating cervix elasticity and length from the cervix stress and strain data, and step 805 of calculating probability of spontaneous preterm delivery with the use of the cervix elasticity and length as inputs to a predictive model.

Additional method steps may include conducting this evaluation multiple times for a pregnant woman beginning from 24 weeks of pregnancy, measurement from four (4) cervix sectors (upper, lower, and lateral right and left), calculating cervix length from ultrasound pulse time-of-flight to internal os surface of the cervix, calculating cervix elasticity based on a finite element model simulation for cervix, comprising a cervix map with a set of sectors with cervix elasticity and length data per every sector, and comprising a predictive model derived from a clinical validation study.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for predicting spontaneous preterm delivery, the method comprising the steps of:

a) providing a cervix probe with a head equipped with a plurality of tactile sensors forming together a flat tactile sensor array, and an ultrasound transducer, said head positioned at an angle to a probe shaft, thereby said probe is configured for an orthogonal contact of the entire flat tactile sensor array with an external cervix surface of a pregnant woman, b) inserting said cervix probe into a vagina to contact said external cervix surface, c) applying cervix deformation at an external cervical wall facing the vagina and adjacent to an external cervical os with said cervix probe, while simultaneously acquiring cervix stress data using all of said plurality of tactile sensors and cervix strain data using said ultrasound transducer, d) calculating cervix elasticity and cervix length using said cervix stress data and said cervix strain data, wherein said cervix elasticity is calculated as a ratio of (i) cervix stress derived from said cervix stress data to (ii) cervix strain derived from changes in ultrasound echo time-of-flight during said cervix deformation, wherein said steps (c) and (d) are performed on four radial sectors of cervix, and e) calculating a probability of spontaneous preterm delivery using a predictive model having as inputs respective cervix elasticity and respective cervix length of four radial sectors of cervix.

2. The method as in claim 1, wherein said steps (b) through (e) are performed on the same pregnant woman repeatedly beginning from about 22 weeks of pregnancy.

3. The method as in claim 1, wherein said step (d) further comprising calculating cervix length from ultrasound pulse time-of-flight from the head of the probe located in contact with said cervix surface at the cervical wall facing the vagina and adjacent to an external cervical os to an internal os surface of said cervix, wherein said time-of-flight is determined from a receive-side ultrasound echo reflected from said internal os surface.

4. The method as in claim 1, wherein said step (e) further comprising calculating said cervix elasticity based on a finite element model simulation for cervix.

5. The method as in claim 1, wherein said step (d) further comprising compiling of a cervix map with a set of sectors each showing said respective cervix elasticity and said cervix length.

6. The method as in claim 1, wherein in said step (e) said predictive model is derived using a clinical validation study.

7. A probe for predicting spontaneous preterm delivery, said probe comprising: a head equipped with a plurality of solely cervix-facing tactile sensors forming together angle to a probe shaft, thereby said probe is configured for detecting cervical wall pressure distribution during an orthogonal contact with and deformation of an external cervical wall adjacent an external cervical os and facing a vagina, while avoiding contact with adjacent vaginal walls, said ultrasound transducer is positioned adjacent to said plurality of tactile sensors on said head, said tactile sensor array is configured to acquire stress data from four radial sectors of cervix, and said ultrasound transducer is configured to emit an ultrasound pulse and to acquire a scattered ultrasound waveform from four radial sectors of cervix during deformation by said head at the external cervical os facing the vagina and without deforming adjacent vaginal walls, a control unit operably connected to said tactile sensor array and said ultrasound transducer and configured for acquiring said stress data from four radial sectors of said cervix using said tactile sensors and said scattered ultrasound waveform from four radial sectors of said cervix using said ultrasound transducer, and a data processor operably connected to said control unit and configured for calculating cervix elasticity and cervix length of four radial sectors of said cervix using said stress data from four radial sectors of said cervix and said ultrasound waveform from four radial sectors of said cervix, wherein (i) cervix length is calculated from receive-side echo time-of-flight to an internal os reflection, and (ii)

cervix elasticity is calculated as ratio of (i) cervix stress derived from stress data to (ii) cervix strain derived from changes in ultrasound eco time-of-flight during said cervix deformation, said processor is further configured to calculate a probability of spontaneous preterm delivery using a predictive model having as inputs of respective cervix elasticity and respective cervix length of four radial sectors of said cervix.

8. The probe as in claim 7, wherein said head further comprises an elastic layer covering said tactile sensor array and said ultrasound transducer to allow reversible stress transmission therethrough and multiple disinfections of said probe.

9. The probe as in claim 7, wherein said ultrasound transducer is made using a piezoceramic composite material with a mylar film with a predetermined thickness as an acoustic matching layer.

10. The probe as in claim 7, wherein said ultrasound transducer has an elastic backing layer to allow attenuation of acoustic backscattering from a support base housing thereof.

11. The probe, as in claim 7, wherein the angle between the head and the probe shaft is between 130 degrees and 150 degrees.

12. The probe, as in claim 7, wherein the plurality of tactile sensors are positioned around the ultrasound transducer and in the same plane therewith at the head of the probe.

13. The probe, as in claim 12, wherein both the head and the probe shaft are straight and form a V-shape in between thereof.

14. The probe, as in claim 13, wherein the probe shaft is no larger than the head of the probe to allow applying of cervix deformation without deforming adjacent vaginal walls at the same time.

* * * * *